(12) United States Patent
Avitall et al.

(10) Patent No.: US 8,784,414 B2
(45) Date of Patent: *Jul. 22, 2014

(54) PRESHAPED LOCALIZATION CATHETER, SYSTEM, AND METHOD FOR GRAPHICALLY RECONSTRUCTING PULMONARY VEIN OSTIA

(71) Applicant: Boston Scientific Scimed, Inc., Maple Grove, MN (US)

(72) Inventors: Boaz Avitall, Whitefish Bay, WI (US); Josef V. Koblish, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/029,438

(22) Filed: Sep. 17, 2013

(65) Prior Publication Data

US 2014/0018797 A1  Jan. 16, 2014

Related U.S. Application Data

(63) Continuation of application No. 11/429,051, filed on May 5, 2006, now Pat. No. 8,535,303.

(60) Provisional application No. 60/678,247, filed on May 5, 2005.

(51) Int. Cl.
*A61B 18/14* (2006.01)

(52) U.S. Cl.
USPC .......................................... 606/41; 604/95.04

(58) Field of Classification Search
USPC ............................................... 606/41, 45–47
See application file for complete search history.

(56) References Cited

U.S. PATENT DOCUMENTS

| 4,650,466 A | 3/1987 | Luther |
| 4,750,671 A | 6/1988 | Heinle et al. |
| 4,882,777 A | 11/1989 | Narula |
| 4,921,484 A | 5/1990 | Hillstead |
| 5,156,151 A | 10/1992 | Imran |
| 5,228,442 A | 7/1993 | Imran |
| 5,239,999 A | 8/1993 | Imran |
| 5,263,493 A | 11/1993 | Avitall |
| 5,279,299 A | 1/1994 | Imran |

(Continued)

FOREIGN PATENT DOCUMENTS

| WO | 9726038 A1 | 7/1997 |
| WO | 0032129 A1 | 6/2000 |

(Continued)

*Primary Examiner* — Linda Dvorak
*Assistant Examiner* — Amanda Scott
(74) *Attorney, Agent, or Firm* — Seager, Tuft & Wickhem, LLC

(57) ABSTRACT

Catheters, systems, and methods are provided for performing medical procedures, such as tissue ablation, adjacent the ostia of anatomical vessels, such as pulmonary veins. The catheter comprises an elongated flexible catheter body, which includes a proximal shaft portion and a distal shaft portion, and a tracking element carried by the distal shaft portion. The proximal section is pre-shaped to form a curve having an apex sized to be inserted into the vessel ostium, and a distal section configured to contact the adjacent tissue when the curve apex is inserted within the vessel ostium. The method may comprise inserting the curve apex into the vessel ostium to place the distal section in contact with a first tissue site adjacent the vessel ostium, and determining a location of the tracking element(s) within a coordinate system while the distal section is in contact with the first tissue site.

19 Claims, 12 Drawing Sheets

(56) References Cited

U.S. PATENT DOCUMENTS

| | | | |
|---|---|---|---|
| 5,327,885 | A | 7/1994 | Griffith |
| 5,368,567 | A | 11/1994 | Lee et al. |
| 5,383,574 | A | 1/1995 | Raphael |
| 5,391,199 | A | 2/1995 | Ben |
| 5,411,546 | A | 5/1995 | Bowald et al. |
| 5,423,772 | A | 6/1995 | Lurie et al. |
| 5,456,667 | A | 10/1995 | Ham et al. |
| 5,456,682 | A | 10/1995 | Edwards et al. |
| 5,505,730 | A | 4/1996 | Edwards |
| 5,571,038 | A | 11/1996 | Halling |
| 5,582,609 | A | 12/1996 | Swanson et al. |
| 5,617,854 | A | 4/1997 | Munsif |
| 5,702,368 | A | 12/1997 | Stevens et al. |
| 5,733,280 | A | 3/1998 | Avitall et al. |
| 5,738,683 | A | 4/1998 | Osypka |
| 5,755,715 | A | 5/1998 | Stern et al. |
| 5,814,028 | A | 9/1998 | Swartz et al. |
| 5,820,591 | A | 10/1998 | Thompson et al. |
| 5,823,955 | A | 10/1998 | Kuck et al. |
| 5,916,214 | A | 6/1999 | Cosio et al. |
| 5,938,660 | A | 8/1999 | Swartz et al. |
| 5,938,694 | A | 8/1999 | Jaraczewski et al. |
| 5,971,983 | A | 10/1999 | Lesh |
| 5,972,019 | A | 10/1999 | Engelson et al. |
| 5,983,126 | A | 11/1999 | Wittkampf et al. |
| 5,991,650 | A | 11/1999 | Swanson et al. |
| 5,993,462 | A | 11/1999 | Pomeranz et al. |
| 6,002,955 | A | 12/1999 | Willems et al. |
| 6,012,457 | A | 1/2000 | Lesh |
| 6,024,740 | A | 2/2000 | Lesh et al. |
| 6,029,671 | A | 2/2000 | Stevens et al. |
| 6,064,902 | A | 5/2000 | Haissaguerre et al. |
| 6,066,126 | A | 5/2000 | Li et al. |
| 6,068,629 | A | 5/2000 | Haissaguerre et al. |
| 6,071,229 | A | 6/2000 | Rubins et al. |
| 6,106,522 | A | 8/2000 | Fleischman et al. |
| 6,164,283 | A | 12/2000 | Lesh |
| 6,214,002 | B1 | 4/2001 | Fleischman et al. |
| 6,224,587 | B1 | 5/2001 | Gibson |
| 6,237,605 | B1 | 5/2001 | Vaska et al. |
| 6,270,496 | B1 | 8/2001 | Bowe et al. |
| 6,287,301 | B1 | 9/2001 | Thompson et al. |
| 6,311,692 | B1 | 11/2001 | Vaska et al. |
| 6,325,797 | B1 | 12/2001 | Stewart et al. |
| 6,464,700 | B1 | 10/2002 | Koblish et al. |
| 6,485,489 | B2 | 11/2002 | Teirstein et al. |
| 6,490,474 | B1 | 12/2002 | Willis et al. |
| 6,529,756 | B1 | 3/2003 | Phan et al. |
| 6,542,781 | B1 | 4/2003 | Koblish et al. |
| 6,545,199 | B1 | 4/2003 | Anderson et al. |
| 6,572,611 | B1 | 6/2003 | Falwell |
| 6,572,612 | B2 | 6/2003 | Stewart et al. |
| 6,628,576 | B1 | 9/2003 | Watanabe et al. |
| 6,652,515 | B1 | 11/2003 | Maguire et al. |
| 6,728,563 | B2 | 4/2004 | Rashidi |
| 6,733,499 | B2 | 5/2004 | Scheib |
| 6,745,080 | B2 | 6/2004 | Koblish |
| 6,869,414 | B2 | 3/2005 | Simpson et al. |
| 6,887,236 | B2 | 5/2005 | Gilboa |
| 6,923,808 | B2 | 8/2005 | Taimisto |
| 6,926,669 | B1 | 8/2005 | Stewart et al. |
| 6,926,714 | B1 | 8/2005 | Sra |
| 6,950,689 | B1 | 9/2005 | Willis et al. |
| 6,973,339 | B2 | 12/2005 | Govari |
| 7,013,619 | B2 | 3/2006 | Hoover |
| 7,101,362 | B2 | 9/2006 | Vanney |
| 8,535,303 | B2 | 9/2013 | Avitall et al. |
| 2001/0007070 | A1 | 7/2001 | Stewart et al. |
| 2001/0039413 | A1 | 11/2001 | Bowe |
| 2003/0069570 | A1 | 4/2003 | Witzel et al. |
| 2003/0093072 | A1 | 5/2003 | Friedman |
| 2003/0130598 | A1 | 7/2003 | Manning et al. |
| 2003/0208102 | A1 | 11/2003 | Gilboa |
| 2004/0034365 | A1 | 2/2004 | Lentz et al. |
| 2004/0106920 | A1 | 6/2004 | Jenkins et al. |
| 2004/0147827 | A1 | 7/2004 | Bowe |
| 2005/0004516 | A1 | 1/2005 | Vanney |
| 2005/0070887 | A1 | 3/2005 | Taimisto et al. |
| 2005/0187455 | A1 | 8/2005 | Rashidi |
| 2005/0197623 | A1 | 9/2005 | Leeflang et al. |
| 2005/0222557 | A1 | 10/2005 | Baxter et al. |
| 2006/0095030 | A1 | 5/2006 | Avitall et al. |
| 2006/0096030 | A1 | 5/2006 | Allen et al. |
| 2006/0241366 | A1 | 10/2006 | Falwell et al. |
| 2011/0114833 | A1 | 5/2011 | Jiang et al. |

FOREIGN PATENT DOCUMENTS

| | | | |
|---|---|---|---|
| WO | 0187174 | A1 | 11/2001 |
| WO | 2004032791 | A2 | 4/2004 |
| WO | 2006012668 | A1 | 2/2006 |

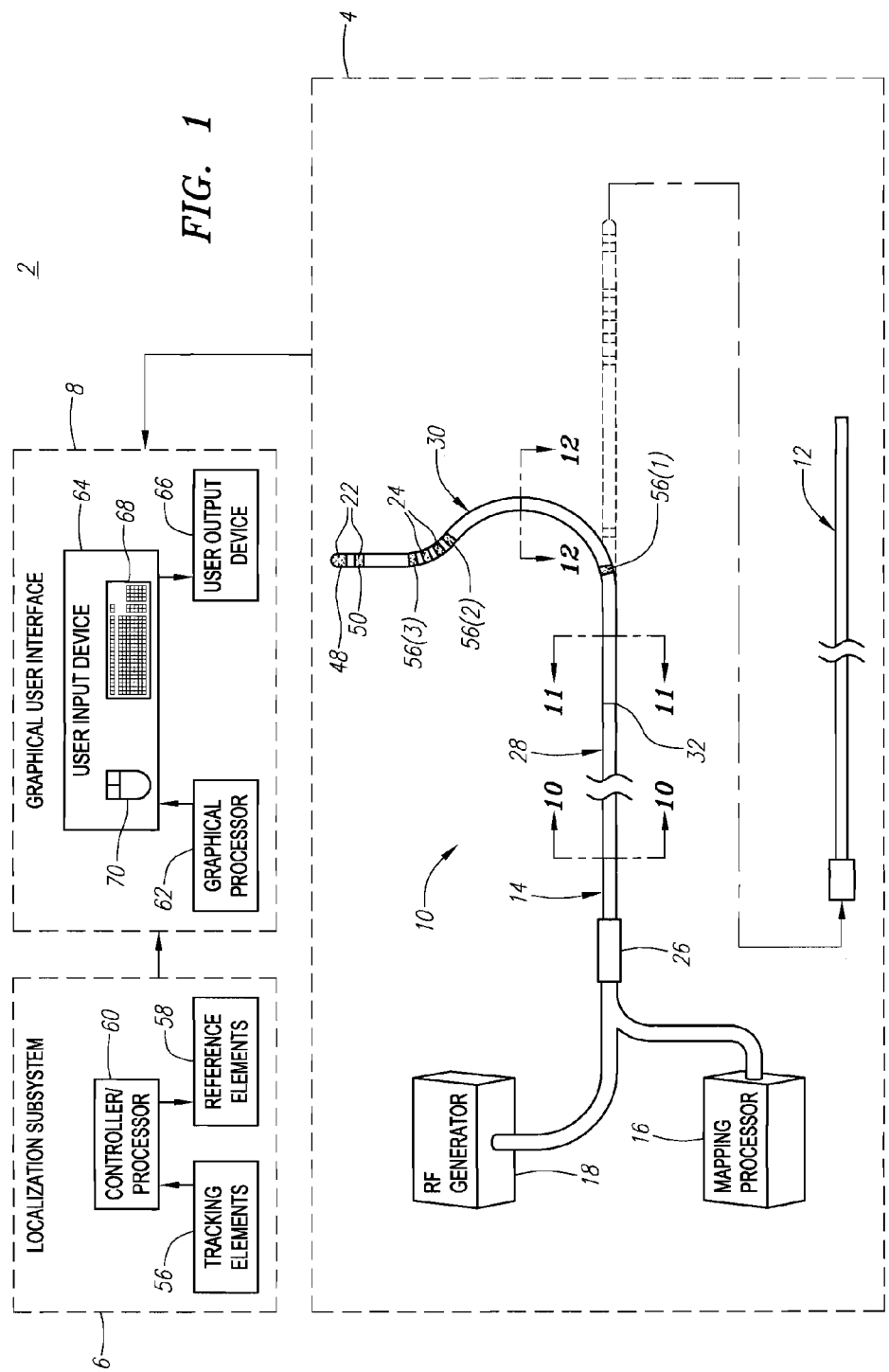

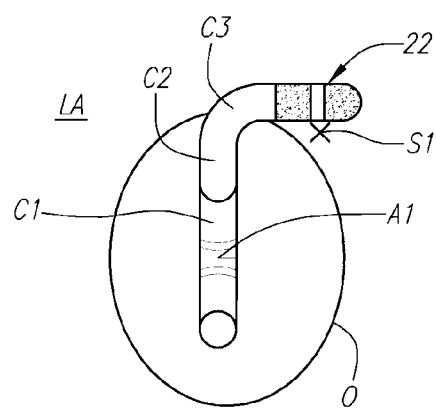
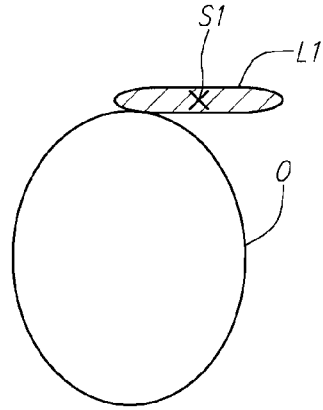
FIG. 17G          FIG. 17H
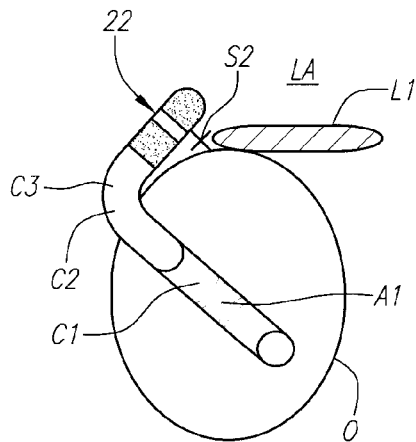
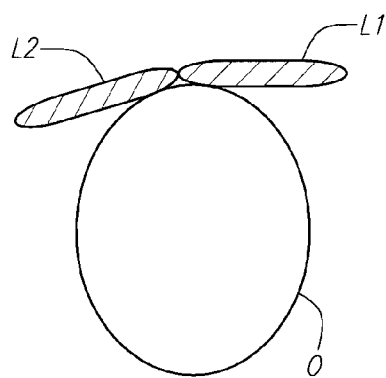
FIG. 17I          FIG. 17J

PRESHAPED LOCALIZATION CATHETER, SYSTEM, AND METHOD FOR GRAPHICALLY RECONSTRUCTING PULMONARY VEIN OSTIA

CROSS REFERENCE TO RELATED APPLICATIONS

This application is a continuation of U.S. application Ser. No. 11/429,051, filed May 5, 2006, now U.S. Pat. No. 8,535,303; which claims priority to U.S. Provisional Patent Application Ser. No. 60/678,247, filed on May 5, 2005; and is related to co-pending U.S. patent application Ser. No. 11/418,757, filed on the same date, the entire disclosures of which are incorporated herein by reference.

FIELD OF THE INVENTION

The present inventions generally relate to systems and methods for treating tissue, and more particularly to systems and methods for ablating tissue in and around the ostia of vessels, such as pulmonary veins, and other anatomical openings.

BACKGROUND OF THE INVENTION

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized manner to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure," which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, not only is the maze procedure technically difficult to do, it also requires open heart surgery and is very expensive.

Maze-like procedures have also been developed utilizing electrophysiology procedures, which involves forming lesions on the endocardium (the lesions being 1 to 15 cm in length and of varying shape) using an ablation catheter to effectively create a maze for electrical conduction in a predetermined path. The formation of these lesions by soft tissue coagulation (also referred to as "ablation") can provide the same therapeutic benefits that the complex incision patterns of the surgical maze procedure presently provides, but without invasive, open heart surgery.

In certain advanced electrophysiology procedures, it is desirable to create a lesions around, within, or otherwise adjacent to orifices. For example, as part of the treatment for certain categories of atrial fibrillation, it may be desirable to create a curvilinear lesion around or within the ostia of the pulmonary veins (PVs), and a linear lesion connecting one or more of the PVs to the mitral valve annulus. Preferably, such curvilinear lesion is formed as far out from the PVs as possible to ensure that the conduction blocks associated with the PVs are indeed electrically isolated from the active heart tissue. To do this, a physician must be able to move the ablation catheter tip along a desired path and either deliver ablative energy while slowly dragging the tip along the path, or deliver energy at a number of discrete points along that path. Either way, it is crucial that the physician be able to accurately and controllably move the catheter tip along that path. When ablating around the PVs, however, energy is typically applied along the curvilinear path using a free-hand approach, thereby rendering it difficult to accurately move the catheter tip along that path. More importantly, during the electrophysiology procedure, it is important to prevent inadvertent damage to non-targeted regions, such as the PVs themselves, which could produce stenosis of the PVs. Thus, it has proven difficult to form circumferential lesions using conventional devices to isolate the PVs and cure ectopic atrial fibrillation.

One technique that has recently been developed to address this problem is disclosed in copending U.S. application Ser. No. 10/983,072, entitled "Preshaped Ablation Catheter for Ablating Pulmonary Vein Ostia within the Heart," which is expressly incorporated herein by reference. In this technique, a proximal section of the distal end of the catheter is formed into a curve and inserted into the pulmonary vein, and then rotated within the pulmonary vein as the ablation catheter tip moves around the ostium in a predictable arc, thereby ensuring that ablations are performed along a desired path on the ostium, while also ensuring that no ablations are performed within the pulmonary vein itself.

While this technique has proven to work fairly well for this intended purpose, it has been discovered that the resiliency of the curve increases the friction between the catheter and the inner surface of the pulmonary vein, thereby causing the curve to grab the inner surface of the pulmonary vein and produce a jerking motion as the curve is rotated within the pulmonary vein. In addition, although ablation lesions can be formed in a predictable manner, such technique does not currently provide a means for verifying proper location of the ablation lesions.

Accordingly, in addition to the need of being able to more efficiently and accurately create circumferential lesions around bodily orifices, such as the ostia of the PVs, there remains a need to be able to allow the curve of a catheter to be more easily rotated within a vessel, as well as a need to provide a means for independently verifying the location of an operative element, such as an tissue ablation element, relative to the ostium of the vessel.

SUMMARY OF THE INVENTION

In accordance with a first aspect of the present inventions, a catheter for performing a medical procedure on tissue adjacent the ostium of an anatomical vessel (e.g., a pulmonary vein) is provided. The catheter comprises an elongated flexible catheter body, which includes a proximal shaft portion and a distal shaft portion, and a tracking element carried by the distal shaft portion. The proximal section is pre-shaped to form a curve having an apex sized to be inserted into the vessel ostium, and a distal section configured to contact the adjacent tissue when the curve apex is inserted within the vessel ostium. By way of non-limiting example, this arrangement allows the location of the tissue adjacent the vessel ostium to be determined.

In one embodiment, the distal section is configured to be placed into a non-radial relationship with the vessel ostium when the curve apex is inserted into the vessel ostium. In the case where tissue ablation is desired, this arrangement allows lesions to be more efficiently formed around the vessel ostium. To provide better contact between the distal section and the adjacent tissue, the distal shaft portion may have a medial section pre-shaped to form another curve that bends in a direction opposite to the curve. To effect the afore-described non-radial relationship between the distal section and the vessel ostium, the first curve can be a simple curve, and the other curve a complex curve that bends in a direction opposite to and out-of-plane with the simple curve. The tracking element(s) may comprise at least three tracking elements. For example, the first tracking element can be carried by the proximal section, the second tracking element can be carried by the medial section, and the third tracking element can be carried by the distal section.

In accordance with a second aspect of the present inventions, a catheter system for performing a medical procedure on tissue adjacent the ostium of an anatomical vessel is provided. The system comprises the aforementioned catheter, and a catheter navigation subsystem configured for determining locations of the tracking element(s) within a coordinate system. In one embodiment, the catheter navigation subsystem is a graphical navigation subsystem configured for graphically reconstructing the vessel ostium based on the determined locations of the tracking element(s). The catheter may comprise a therapeutic or diagnostic element carried by the distal section, in which case, the catheter navigation subsystem may be configured for determining a location of the diagnostic or therapeutic element based on the determined location of the tracking element(s).

In accordance with a third aspect of the present inventions, a method of performing a medical procedure adjacent the vessel ostium using the afore-described catheter is provided. The method comprises inserting the curve apex into the vessel ostium to place the distal section in contact with a first tissue site adjacent the vessel ostium, and determining a location of the tracking element(s) within a coordinate system while the distal section is in contact with the first tissue site. The method may further comprise rotating the vessel curve within the vessel about the apex to place the distal section in contact with a second tissue site adjacent the vessel ostium, and determining another location of the tracking element(s) within the coordinate system while the distal section is in contact with the second tissue site.

In accordance with a fourth aspect of the present inventions, a method of performing a medical procedure on an anatomical vessel (e.g., a pulmonary vein) using a catheter having a proximal section and a distal section is provided. The method comprises forming the proximal section into a curve having an apex. For example, the proximal section may be formed into the curve using a steering mechanism, or the proximal section may be pre-shaped, in which case, it can be formed into the curve by removing a sheath from the proximal section. The method further comprises inserting the apex into an ostium of the vessel to place the distal section in contact with a first tissue site adjacent vessel ostium, and determining a location of the distal section within a coordinate system while contacting the first tissue site. The method may optionally comprise rotating the curve within the vessel about the apex to place the distal section in contact with a second tissue site adjacent the vessel ostium, and determining another location of the distal section within the coordinate system while contacting the second tissue site. By way of non-limiting example, the location(s) of the distal section can be determined by transmitting signals to or from a tracking element carried by the distal section.

In one optional method, the distal section is placed into a non-radial relationship with the vessel ostium when the apex of the curve is inserted into the vessel ostium, so that in the case where tissue ablation is desired, lesions can be more efficiently formed around the vessel ostium. To provide better contact between the distal section and the adjacent tissue, the distal shaft portion may have a medial section, in which case, the method may further comprise forming the other medial section into another curve that bends in a direction opposite the first curve. To effect the afore-described non-radial relationship between the distal section and the vessel ostium, the first curve can be a simple curve, and the other curve can be a complex curve that bends in a direction opposite to and out-of-plane with the simple curve. The tracking element(s) may comprise at least three tracking elements. For example, the first tracking element can be carried by the proximal section, the second tracking element can be carried by the medial section, and the third tracking element can be carried by the distal section.

One optional method comprises graphically reconstructing the vessel ostium based on the determined location of the distal section. In another optional method, the catheter may comprise a therapeutic or diagnostic element carried by the distal section, in which case, the method may further comprise determining a location of the diagnostic or therapeutic element based on the determined location of the distal section. For example, if the therapeutic or diagnostic element comprises a tissue ablative element, the method may further comprise delivering ablation energy to the ablative element to create a lesion at the first tissue site. In this case, the method may further comprise graphically generating a mark representing the lesion at the first tissue site. As another example, if the therapeutic or diagnostic element comprises a tissue mapping element, the method may further comprise receiving mapping signals from the mapping element to create a mapping data point at the first tissue site.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 1 is a plan view of one preferred embodiment of a tissue ablation system constructed in accordance with the present inventions;

FIGS. 17A-17J are plan views of a method of using the tissue treatment system of FIG. 1 to create a circumferential lesion around the ostium of a pulmonary vein.

DETAILED DESCRIPTION OF THE PREFERRED EMBODIMENTS

Figure 17A:
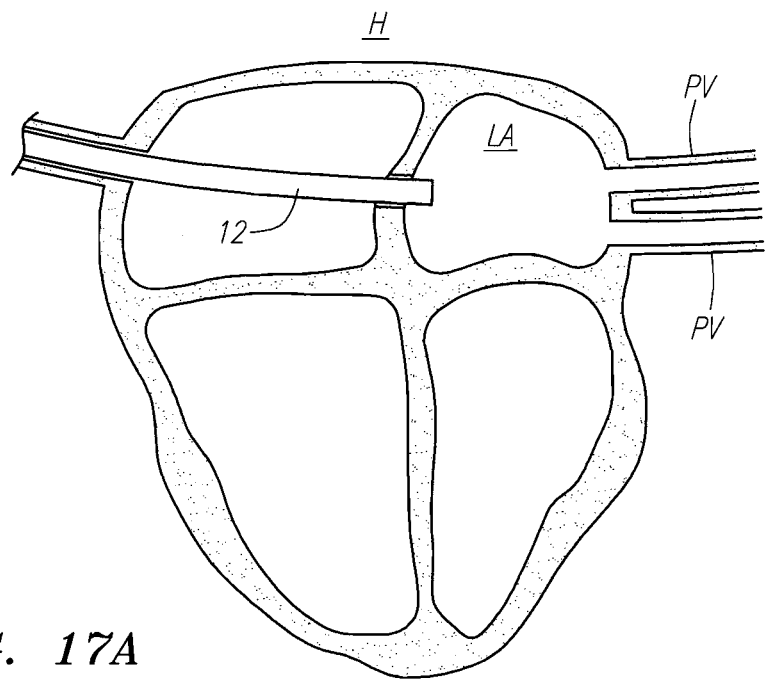
Figure 17B:
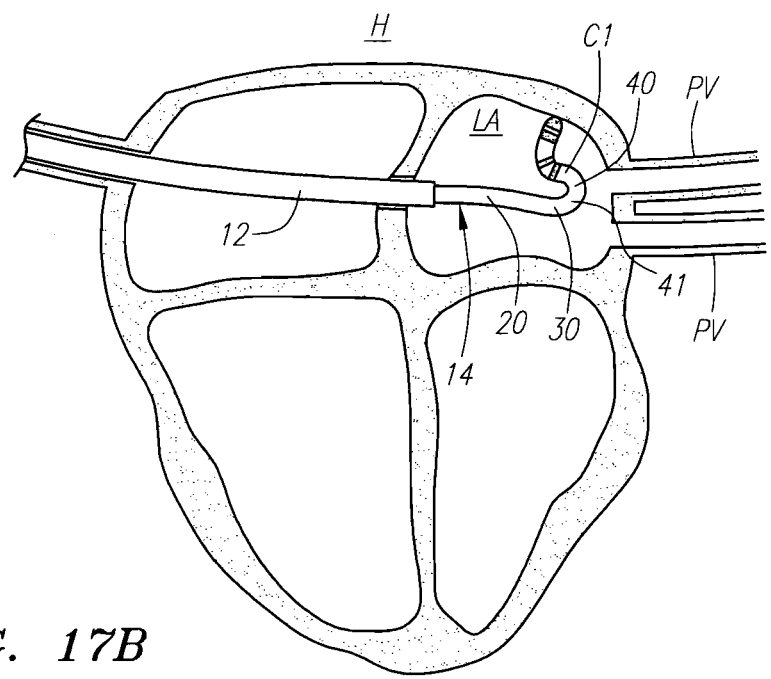
Figure 17C:
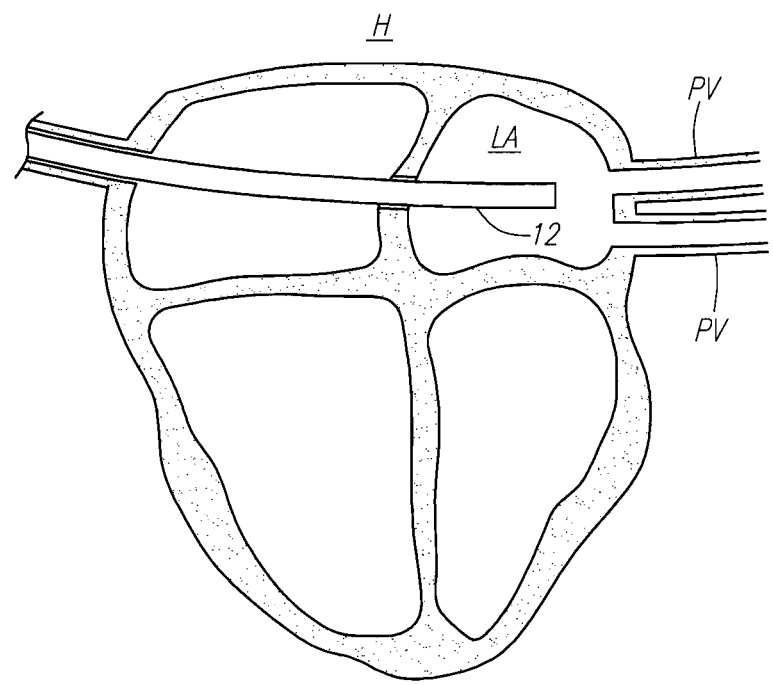
Figure 17D:
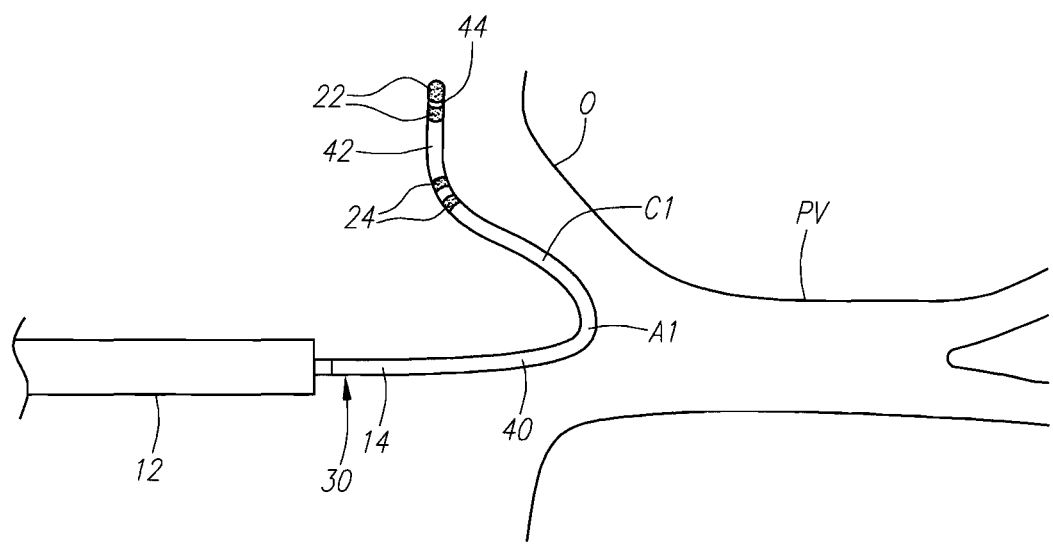
Figures 1, 17E:
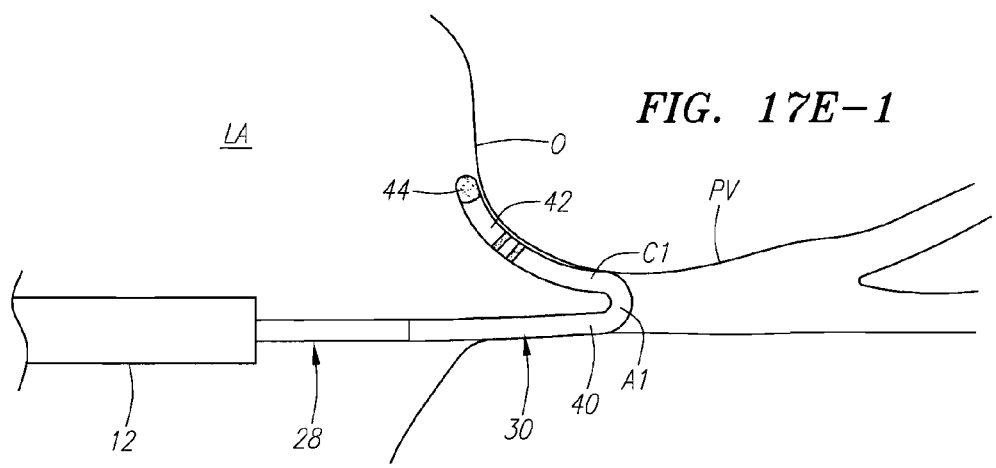
Figures 2, 17E:
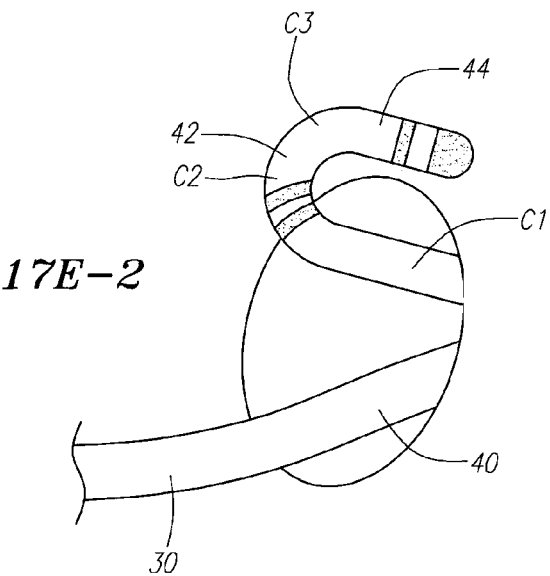
Figures 1, 17F:
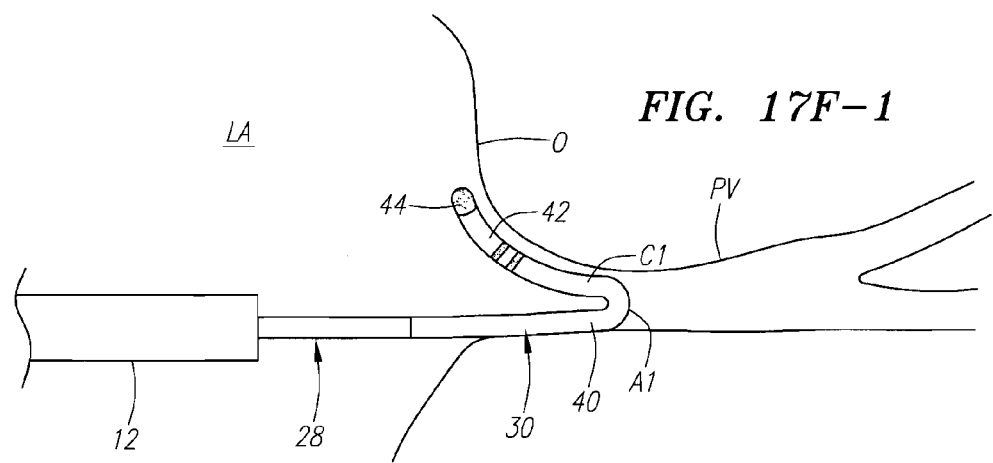
Figures 2, 17F:
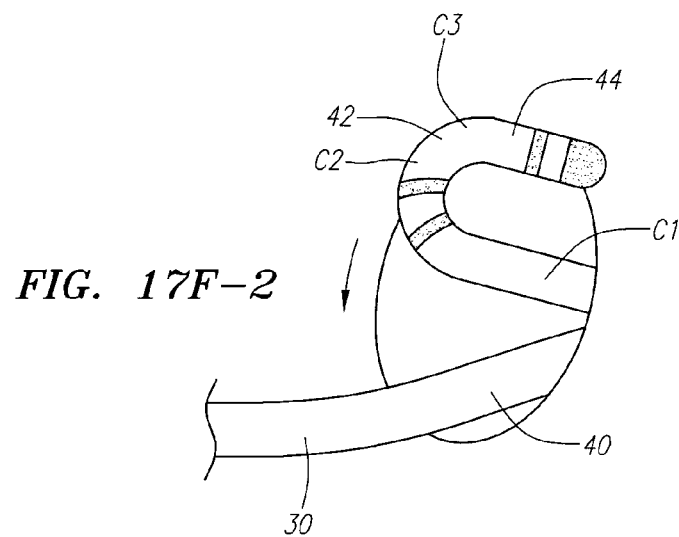

Referring to FIG. 1, an exemplary tissue ablation system 2 constructed in accordance with the present inventions is shown. The system 2 may be used within body lumens, chambers or cavities for therapeutic and diagnostic purposes in those instances where access to interior bodily regions is obtained through, for example, the vascular system or alimentary canal and without complex invasive surgical procedures. For example, the system 2 has application in the diagnosis and treatment of arrhythmia conditions within the heart. The system 2 also has application in the treatment of ailments of the gastrointestinal tract, prostrate, brain, gall bladder, uterus, and other regions of the body. As an example, the system 2 will be described hereinafter for use in pulmonary veins, and specifically, to electrically isolate one or more arrhythmia causing substrates within the ostium of a pulmonary vein from the left atrium of the heart in order to treat ectopic atrial fibrillation.

The medical system 2 generally comprises (1) a ablation/mapping subsystem 4 for mapping and ablating tissue within the heart; (2) a localization subsystem 6 for registering mapping data and the movement of a probe within a three-dimensional coordinate system; and (3) a graphical user interface 8 configured for generating and displaying graphics of the heart and associated anatomical structures, mapping data, and probe within the three-dimensional coordinate system. It should be noted that the elements illustrated in FIG. 1 are functional in nature, and are not meant to limit the structure that performs these functions in any manner. For example, several of the functional blocks can be embodied in a single device, or one of the functional blocks can be embodied in multiple devices. Also, the functions can be performed in hardware, software, or firmware.

I. Ablation/Mapping Subsystem

The ablation/mapping subsystem 4 is configured to identify and treat a target tissue site or sites, e.g., aberrant conductive pathways. To this end, the ablation/mapping subsystem 4 comprises a conventional guide sheath 12 and an ablation/mapping catheter 14 that can be guided through the guide sheath 12. As will be described in further detail below, the ablation/mapping catheter 14 is configured to be introduced through the vasculature of the patient, and into the left atrium of the heart, where it can be used to ablate and map heart tissue within and/or around the ostia of selected pulmonary veins. The ablation/mapping subsystem 4 also comprises a mapping processor 16 and a source of ablation energy, and in particular, a radio frequency (RF) generator 18. Although the mapping processor 16 and RF generator 18 are shown as discrete components, they can alternatively be incorporated into a single integrated device.

A. Mapping Processor

The mapping processor 16 is configured to detect, process, and record electrical signals within the heart, and specifically, electrical signals adjacent the ostia of the pulmonary vein. Based on these electrical signals, a physician can identify the specific target tissue sites adjacent the pulmonary vein ostia to be ablated, and to ensure that the arrhythmia causing substrates within the pulmonary vein ostia have been electrically isolated by the ablative treatment. Such mapping techniques are well known in the art, and thus for purposes of brevity, will not be described in further detail.

B. RF Generator

The RF generator 18 is configured to deliver ablation energy to the ablation/mapping catheter 14 in a controlled manner in order to ablate the target tissue sites identified by the mapping processor. Alternatively, other types of ablative sources besides the RF generator 18 can be used, e.g., a microwave generator, an ultrasound generator, a cryoablation generator, and a laser or other optical generator. Ablation of tissue within the heart is well known in the art, and thus for purposes of brevity, the RF generator 18 will not be described in further detail. Further details regarding RF generators are provided in U.S. Pat. No. 5,383,874, which is expressly incorporated herein by reference.

C. Guide Sheath

The ablation/mapping catheter 14 may be advanced though the guide sheath 12 to the target location. The sheath 12, which should be lubricious to reduce friction during movement of the ablation/mapping catheter 14, may be advanced over a guidewire in conventional fashion. Alternatively, a steerable sheath may be provided. With respect to materials, the proximal portion of the sheath 12 is preferably a Pebax® material and stainless steel braid composite, and the distal portion is a more flexible material, such as unbraided Pebax®, for steering purposes. The sheath 12 should also be stiffer than the ablation/mapping catheter 14. A sheath introducer (not shown), such as those used in combination with basket catheters, may be used when introducing the ablation/mapping catheter 14 into the sheath 12. The guide sheath 12 preferably includes a radio-opaque compound, such as barium, so that the guide sheath 12 can be observed using fluoroscopic or ultrasound imaging, or the like. Alternatively, a radio-opaque marker (not shown) can be placed at the distal end of the guide sheath 12.

D. Ablation/Mapping Catheter

The ablation/mapping catheter 14 comprises an integrated flexible catheter body 20, a plurality of distally mounted operative elements, and in particular, a tissue ablative element 22 and a mapping element 24, and a proximally mounted handle 26. The catheter body 20 comprises a proximal member 28 and a distal member 30 that are preferably either bonded together at an interface 32 with an overlapping thermal bond or adhesively bonded together end to end over a sleeve in what is referred to as a "butt bond." Alternatively, the integrated catheter body 20 may not have separate proximal and distal members 28, 30 that are subsequently integrated together, but instead, may have an unibody design.

Figure 10:
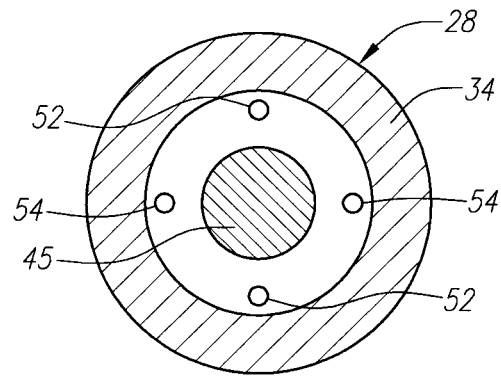
FIG. 10 is a cross-sectional view of the ablation/mapping catheter, taken along the line 10-10 of FIG. 1.
Figure 11:
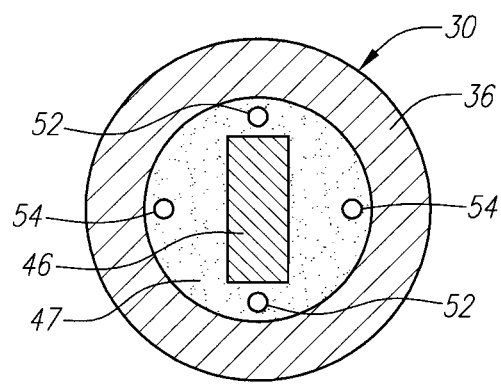
FIG. 11 is a cross-sectional view of the ablation/mapping catheter of FIG. 2, taken along the line 11-11 of FIG. 1.
Figure 12:
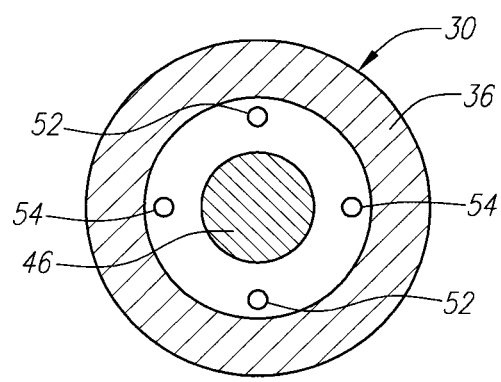
FIG. 12 is a cross-sectional view of the ablation/mapping catheter of FIG. 2, taken along the line 12-12 of FIG. 1.

The catheter body 20 is preferably about 5 French to 9 French in diameter, with the proximal member 28 being relatively long (e.g., 80 to 100 cm), and the distal member 30 relatively short (e.g., 3.5 cm to 10.5 cm). As best illustrated in FIG. 10, the proximal member 28 comprises a tubular body 34 that is preferably formed from a biocompatible thermoplastic material, such as a Pebax® material (polyether block amide) and stainless steel braid composite, which has good torque transmission properties. In some implementations, an elongate guide coil (not shown) may also be provided within the proximal member 28. As best illustrated in FIGS. 11 and 12, the distal member 30 comprises a tubular body 36 that is preferably formed from a softer, more flexible biocompatible thermoplastic material such as unbraided Pebax® material, polyethylene, or polyurethane. The distal member 30 preferably includes a radio-opaque compound, such as barium, so that the catheter body 20 can be observed using fluoroscopic or ultrasound imaging, or the like. Alternatively, radio-opaque markers (not shown) can be placed along the distal member 30.

The catheter body 20 has a resilient shape that facilitates the functionality of the ablation/mapping catheter 14. In particular, and as is standard with most catheters, the proximal member 28 has an unconstrained straight or linear geometry to facilitate the pushability of the ablation/mapping catheter 14 through the guide sheath 12. To this end, the proximal member 28 further comprises a resilient, straight center support 45 positioned inside of and passing through the length of the proximal tubular body 34. In the illustrated embodiment, the proximal center support 45 is a circular element formed from resilient inert wire, such as nickel titanium (commercially available under the trade name nitinol) or 17-7 stainless steel wire. Resilient injection molded plastic can also be used. The diameter of the proximal center support 45 is preferably between about 0.35 mm to 0.80 mm.

Figure 13:
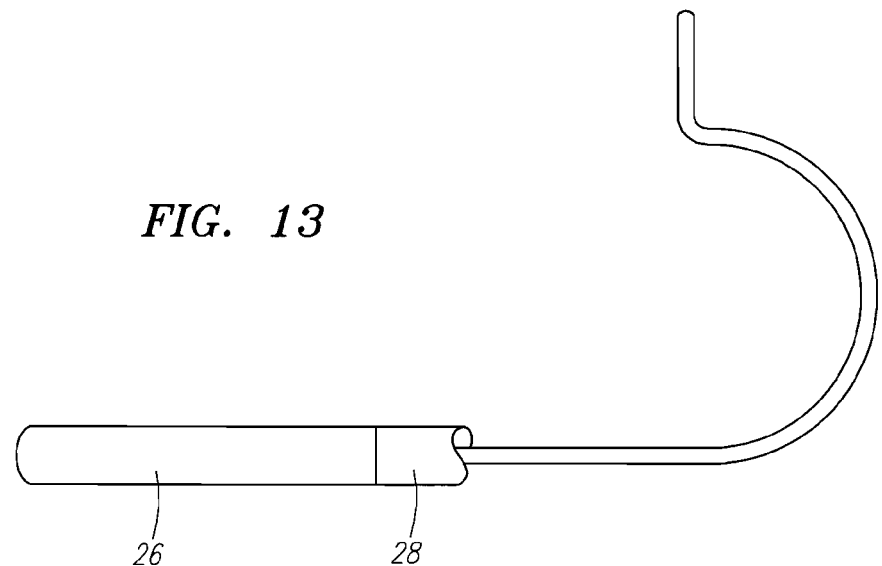
FIG. 13 is a partially cutaway view of the distal end of the ablation/mapping catheter of FIG. 2, particularly showing one means for internally actuating the catheter.

In contrast, the distal member 30 is configured to be alternately placed between a linear geometry (shown in phantom in FIG. 1) and an expanded geometry. The shape of the distal member 30 is achieved through the use of a center support 46 that is positioned inside of and passes through the length of the distal tubular body 36, as illustrated in FIG. 13. In the illustrated embodiment, the distal center support 46 is similar to the proximal center support 45 in composition and dimension. To improve the torqueability of the distal member 30, which is important to the predictable and controlled movement of the distal member 30, the distal center support 46 is preferably affixed within the distal portion of the proximal member 28 (such as by soldering the proximal end of the distal center support 46 to the distal end of the proximal center support 45), so that the torsional force applied to the proximal member 28 is transmitted to the distal member 30 without significant loss. Alternatively, the center supports 45, 46 can be formed of a unibody structure. To further improve the torqueability of the distal member 30, the proximal end of the center support 46 can be flattened into a rectangular cross-sectional geometry, as illustrated in FIG. 11. In addition, a filler material, such as epoxy 47, can be injected into the proximal end of the distal tubular body 36 in order to integrate all of the internal components of the distal member 30 together to further improve the torqueability at the junction between the proximal and distal members 28, 30.

Additional details concerning the placement of a center support within the distal member of a catheter can be found in U.S. Pat. No. 6,287,301, which is expressly incorporated herein by reference. In alternative embodiments, a stylet, instead of the center supports 45, 46, can be used. In this case, the stylet can be removably inserted through a lumen (not shown) formed through the catheter body 20 to place the distal member 30 into its expanded geometry.

Figure 2:
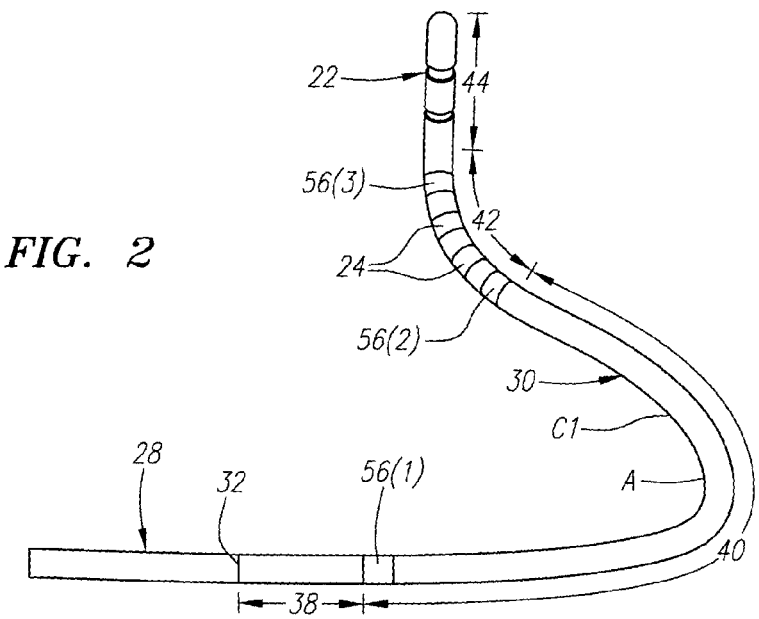
FIG. 2 is a perspective view of the distal end of an ablation/mapping catheter used in the tissue ablation system of FIG. 1.
Figure 3:
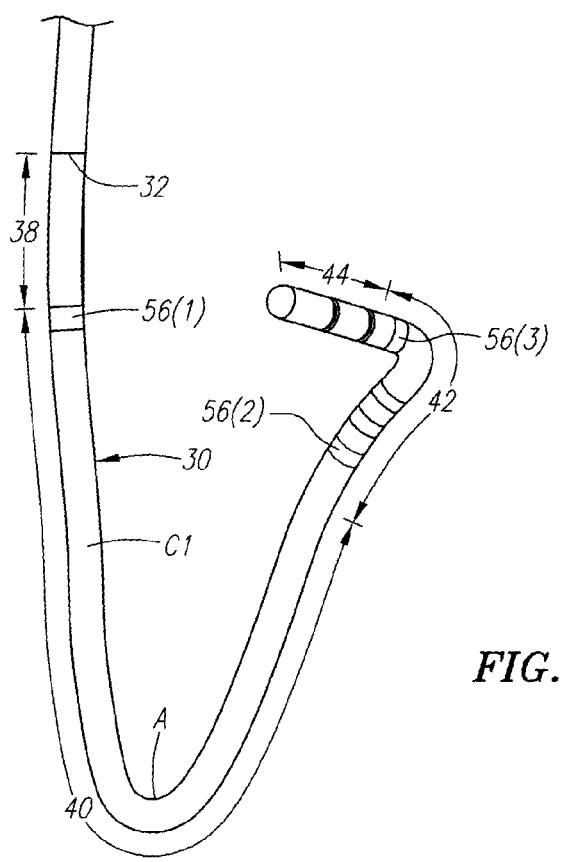
FIG. 3 is another perspective view of the distal end of the ablation/mapping catheter of FIG. 2.

As best shown in FIGS. 2 and 3, the distal member 30 has four geometrically distinct sections: (1) a shaft transition section 38 that distally extends from the proximal member 28; (2) a proximal section 40 that distally extends from the shaft transition section 38 and serves to provide an anchoring point within the vessel ostium around which the ablative/mapping elements 22, 24 can be positioned; (3) a medial section 42 that distally extends from the proximal section 40 and serves to properly locate the distal section 44 relative to the tissue outside of the vessel ostium; and (4) a distal section 44 that distally extends from the medial section 42 and serves to carry the ablative element 22. The distal member 30 is uniquely shaped to perform the aforementioned functions.

In particular, referring further to FIGS. 2-6, the shaft transition section 38 is pre-shaped into a straight geometry. In the illustrated embodiment, the proximal member 28 and transition section 38 of the distal member 30 are collinear (i.e., the proximal member 28 and transition section 38 are not angled relative to each other). In this manner, bending forces that would otherwise be applied at the interface 32 between the proximal and distal members 28, 30 are minimized, thereby allowing more axial force to be applied to the ablation/mapping catheter 12 without collapsing the distal member 30 onto the proximal member 28 when proximal resistance is applied to the distal member 30. Such proximal resistance would typically be encountered within placing the distal member 30 within the ostium of a vessel, as will be described in further detail below.

Figure 4:
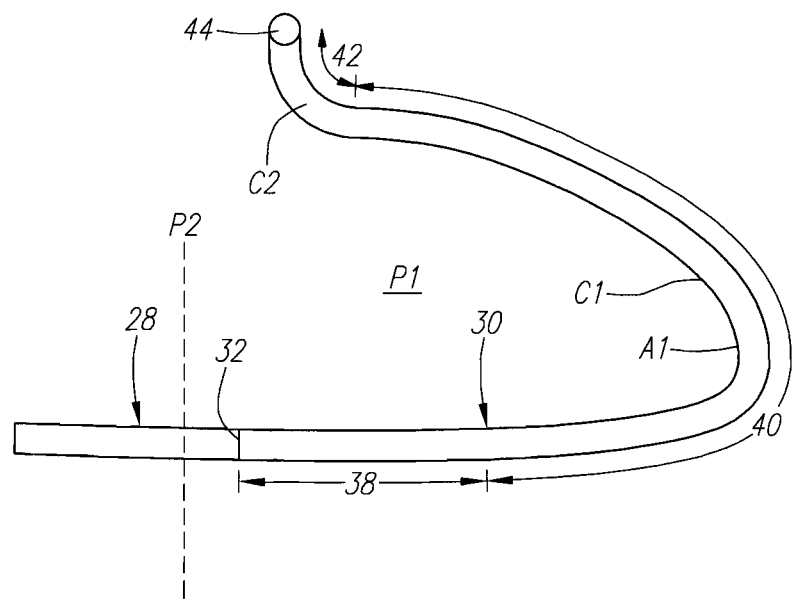
FIG. 4 is a plan view of the distal end of the ablation/mapping catheter of FIG. 2.
Figure 5:
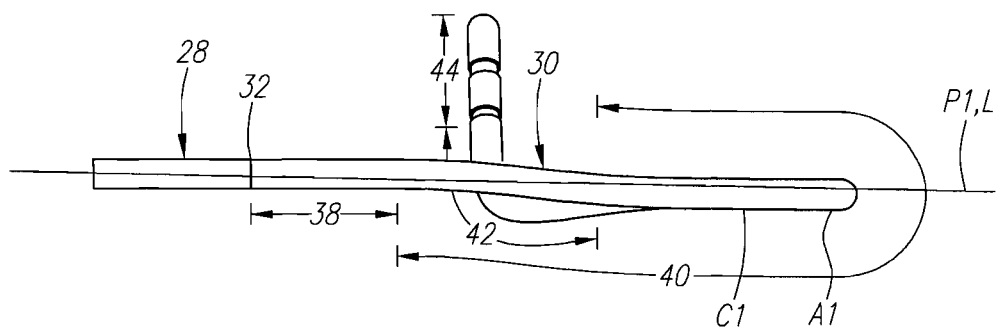
FIG. 5 is a profile view of the distal end of the ablation/mapping catheter of FIG. 2.

As best illustrated in FIG. 4, the proximal section 40 is configured to be internally actuated from a straight geometry to form a simple curve C1 (i.e., a curve that lies in a single plane, and in this case, plane P1 as illustrated in FIG. 5) in the absence of an external force (e.g., the force of gravity and the compressive force otherwise applied to the distal member 30 by the guide sheath 14). In the embodiment illustrated in FIG.

Figure 7:
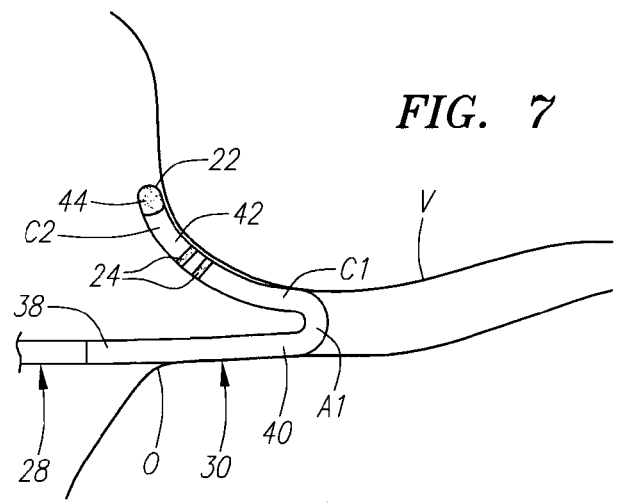
FIG. 7 is a side view of the distal end of the ablation/mapping catheter of FIG. 2, particularly shown inserted into the ostium of a pulmonary vein.
Figures 8, 9:
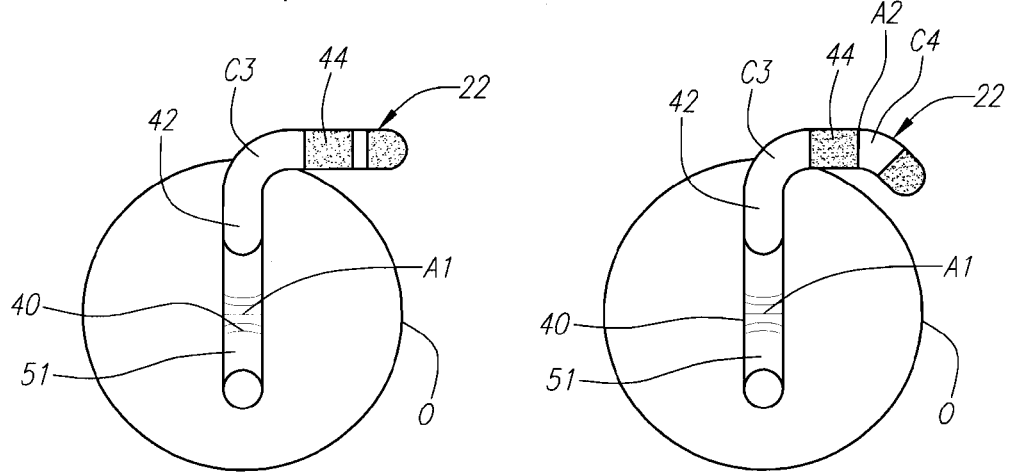
FIG. 8 is a front view of the distal end of the ablation/mapping catheter of FIG. 2, particularly shown inserted into the ostium of a pulmonary vein.
FIG. 9 is a front view of the distal end of an alternative ablation/mapping catheter that can be used in the tissue ablation system of FIG. 2, particularly shown inserted into the ostium of a pulmonary vein.

1, internal actuation of the proximal section 40 is accomplished by pre-shaping the proximal section 40 into the desired curve, and in particular, by incorporating the pre-shaped center support 46 into the distal member 30, as discussed above. The particular unconstrained shape of the proximal section 40 is such that an apex A1 of the simple curve C1 can be conveniently inserted into the ostium O of an anatomical vessel V, as illustrated in FIGS. 7 and 8. Preferably, to facilitate this insertion, the simple curve C1 bends more than 70 degrees, preferably more than 90 degrees, and more preferably, greater than 135 degrees. However, the bend of the simple curve C1 is preferably not so great that the proximal section 40 does not intersect itself.

The medial section 42 is configured to be internally actuated from a straight geometry to form a complex curve (i.e., a curve that can be projected onto more than one plane) in the absence of an external force, and in particular, a compressive force. In the embodiment illustrated in FIG. 1, internal actuation of the medial section 42 is accomplished by pre-shaping the medial section 42 into the desired curve, as will be described in further detail below. The particular unconstrained shape of the medial section 42, is such, that it bends opposite to and out-of-plane with the simple curve C1. That is, the complex curve has a proximal curve C2 that, when projected onto the plane P1 (see FIG. 4), bends opposite to the simple curve C1, and a distal curve C3 that, when projected on a plane P2 that is perpendicular to the longitudinal axis L of the proximal member 28 (see FIG. 6), bends out of the plane PL. As will be described in further detail below, the proximal projected curve C2 serves to properly locate the distal section 44 into contact with the tissue located outside of the vessel ostium O, as illustrated in FIG. 7. The distal projected curve C3 serves to place the distal section 44 into a non-radial relationship (i.e., oblique or tangential) with the vessel ostium O, as illustrated in FIG. 8.

In the illustrated embodiment, the proximal projected curve C2 has a 90 degree bend, so that the distal section 44 can be placed firmly against the tissue surrounding the vessel ostium O, as illustrated in FIG. 7. Alternatively, the proximal projected curve C2 can have a greater than 90 degree bend to maximize the contact between the distal section 44 and the surrounding tissue, but preferably does not exceed 135 degrees to minimize any chance that the distal section 44 may enter into the vessel ostium O. In the illustrated embodiment, the distal projected curve C3 has a 90 degree bend, so that the distal section 44 is arranged tangentially relative to the vessel ostium O, as illustrated in FIG. 8. Alternatively, the distal projected curve C3 may have any bend that arranges the distal section 44 obliquely relative to the vessel ostium, but preferably falls within the range of 60 to 120 degrees, so that the oblique relationship of the distal section 44 falls within the range of −30 to 30 degrees from the tangent. In this manner, the distal section 44 spans as much of the tissue surrounding the vessel ostium O as possible.

Figure 6:
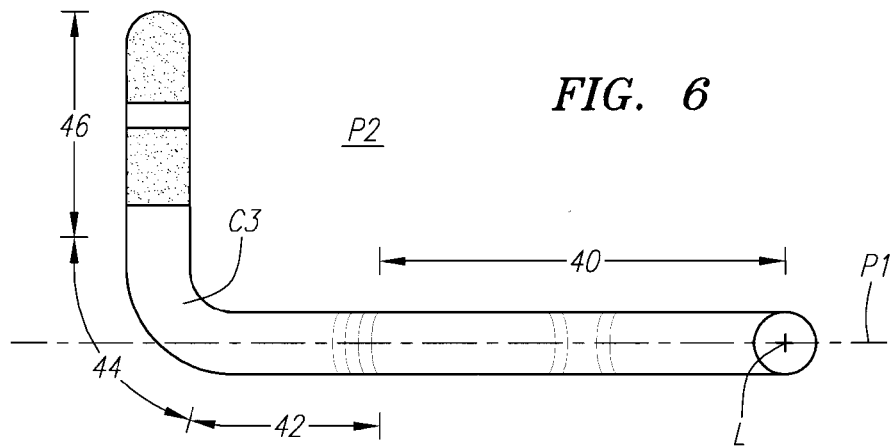
FIG. 6 is another profile view of the distal end of the ablation/mapping catheter of FIG. 2.

As best illustrated in FIGS. 5 and 6, the distal section 44 is pre-shaped into a straight geometry. Alternatively, the distal section 44 may be pre-shaped into a curved geometry. In this case, the distal section 44 preferably forms a simple curve C4 having an apex A2 that points away from the longitudinal axis L1 of the proximal member 28, as illustrated in FIG. 9. In this manner, the shape of the distal section 44 will conform better with the perimeter of the vessel ostium O. Notably, such a configuration will form the ablative element 22 into a curvilinear ablative element (as opposed to a linear ablative element that would be formed when mounted on a catheter section that is straight).

Figure 14:
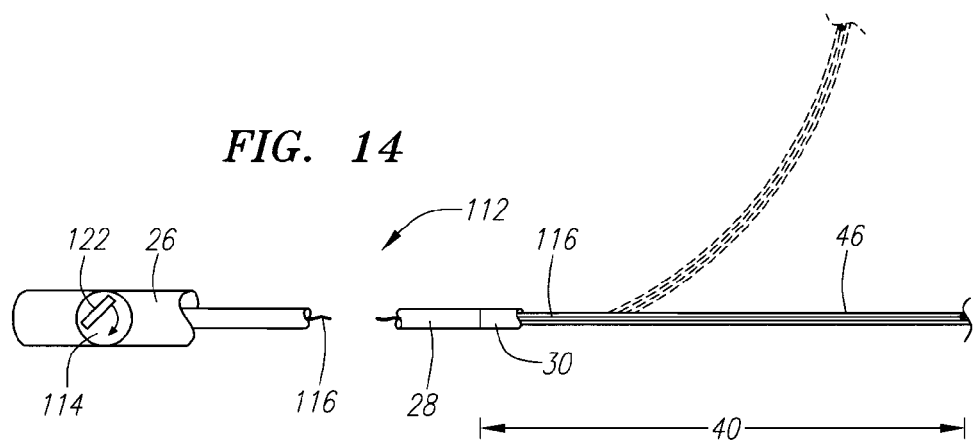
FIG. 14 is a partially cutaway view of the distal end of an alternative ablation/mapping catheter than can be used in the tissue ablation system of FIG. 1, particularly showing another means for internally actuating the catheter.

Alternatively, rather than pre-shaping the proximal section 40 of the distal member 30, a steering mechanism may be used to bend the proximal section 40. In particular, FIG. 14 illustrates an ablation/mapping catheter 112 that is similar to the previously described catheter 12, with the exception that a steering mechanism is used to transform the proximal section 40 of the distal member 28 from its straight geometry into its curved geometry, as illustrated in FIG. 14. In particular, the catheter 112 comprises a steering mechanism 114 that is incorporated into the handle 26, and a steering wire 116 with its proximal end attached to the steering mechanism 114 and its distal end connected to the center support 46 at the interface between the proximal and medial sections 40, 42 of the distal member 30. The steering wire 116 is attached to the side of the center support 46 that faces the direction in which the proximal section 40 of the distal member 30 is configured to curve or bend (as shown in phantom).

Figure 15:
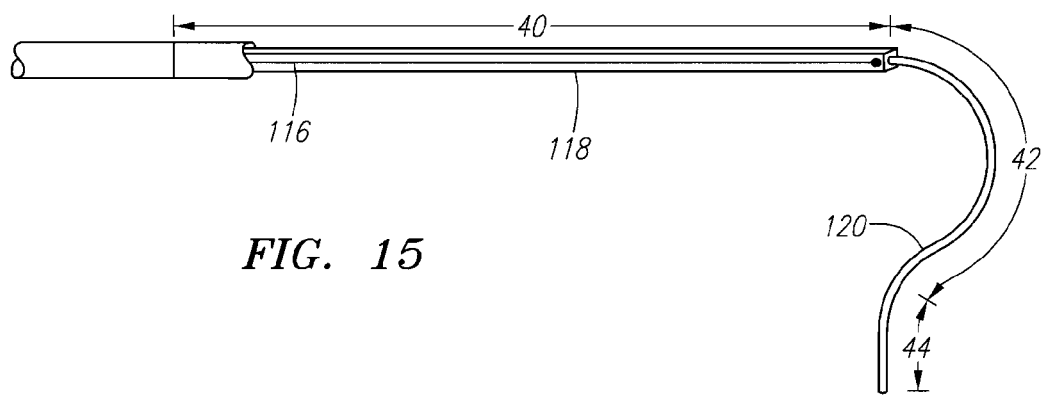
FIG. 15 is a partially cutaway view of the distal end of another alternative ablation/mapping catheter than can be used in the tissue ablation system of FIG. 1, particularly showing still another means for internally actuating the catheter.

Alternatively, as illustrated in FIG. 15, a center support 118 that terminates at the interface between the proximal and medial sections 40, 42 of the distal member 30 can be used, in which case, a resilient wire 120, which is suitably mounted to the distal end of the center support 46, can be used to pre-shape the intermediate/distal sections 42, 44, as described above. In this case, the center support 46 can be designed to provide the catheter 112 with steering capability independent of the design constraints imposed by pre-shaping the intermediate/distal sections 42, 44.

In any event, the steering mechanism 114 comprises a rotatable steering lever 122, which when rotated in one direction, tensions the steering wire 116, thereby flexing the center support 46, and thus the proximal section 40 of the distal member 30, into the desired curve (shown in phantom). In contrast, rotation of the steering lever 122 in the opposite direction provides slack in the steering wire 116, thereby allowing the resiliency of the center support 46 to flex the proximal section 40 of the distal member 30 back into a straight geometry. Alternatively, the steering lever may be of the sliding type, wherein rearward movement of the steering lever flexes the center support 46, and thus the proximal section 40 of the distal member 30, into the desired curve, and forward movement of the steering lever allows the resiliency of the center support 46 to flex the proximal section 40 of the distal member 30 back into the straight geometry. Steering mechanisms for bending the distal ends of the catheters are well known in the prior art, and thus need not be described in further detail.

It should be appreciated that the use of a steering mechanism has the added advantage of providing a means for optionally reducing the radius of curvature of the simple curve C1 to facilitate its rotation within the pulmonary vein, as will be described in further detail below. In an optional embodiment, the proximal section 40 is both pre-shaped and deflected using a steering mechanism. This is particularly advantageous in that the rigidity and torqueability of the distal member 30 need not be decreased to facilitate full bending of the proximal section 40 by the steering mechanism. That is, typically, in a catheter where only a steering mechanism is used to deflect the catheter, the distal catheter end must be made as flexible as possible in order to achieve the desired bend within the catheter. However, because, in the optional embodiment, the proximal section 40 is pre-shaped to form the desired bend (i.e., the simple C1), the distal member 30 can be relatively stiff, thereby providing for better control of the distal member 30, and allowing the natural resiliency of the distal member 30 to facilitate anchoring of the proximal section 40 within the pulmonary vein. The addition of the steering mechanism provides the added benefit of optionally decreasing the radius of curvature of the simple curve C1 as briefly discussed above, and which will be described in further detail below.

As briefly discussed above with respect to FIG. 1, the ablation/mapping catheter 12 comprises a tissue ablative element 22, which is mounted on the distal member 30 of the catheter body 20. In the illustrated embodiment, the ablative element 22 takes the form of a linear electrode assembly that includes a cap electrode 48 mounted to the distal tip of the distal member 30 and a ring electrode 50 mounted on the distal section 44 of the distal member 30 just proximal to the cap electrode 48.

Notably, the split nature of the ablative element 22 provides selective monopolar and bipolar functionality to the catheter 12. That is, one or both of the tip/ring electrodes 48, 50 can be configured as one pole of a monopolar arrangement, so that ablation energy emitted by one or both of the electrodes 48, 50 is returned through an indifferent patch electrode (not shown) externally attached to the skin of the patient; or the tip/ring electrodes 48, 50 can be configured as two poles of a bipolar arrangement, in which energy emitted by one of the tip/ring electrodes 48, 50 is returned to the other electrode. In addition to serving as a selective unipolar/bipolar means of ablation, the tip/ring electrodes 48, 50 may also serve as a closely spaced high resolution pair of mapping electrodes. The combined length of the ablation electrodes 48, 50 is preferably about 6 mm to about 10 mm in length. In one embodiment, each ablation electrode is about 4 mm in length with 0.5 mm to 3.0 mm spacing, which will result in the creation of continuous lesion patterns in tissue when coagulation energy is applied simultaneously to the electrodes 48, 50.

The ablation electrodes 48, 50 may take the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel or, titanium can be applied. Any combination of the electrodes can also be in the form of helical ribbons or formed with a conductive ink compound that is pad printed onto a nonconductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The ablation electrodes 48, 50 can alternatively comprise a porous material coating, which transmits coagulation energy through an electrified ionic medium. For example, as disclosed in U.S. Pat. No. 5,991,650, ablation electrodes may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

The ablation electrodes 48, 50 are electrically coupled to individual wires 52 (shown in FIGS. 10-12) to conduct ablation energy to them. The wires 52 are passed in conventional fashion through a lumen extending through the associated catheter body, where they are electrically coupled either directly to a connector (not shown) that is received in a port on the handle 26 or indirectly to the connector via a PC board (not shown) in the handle 26. The connector plugs into the RF generator 18 (shown in FIG. 1). Although ablation electrodes 48, 50 have been described as the operative elements that create the lesion, other operative elements, such as elements for chemical ablation, laser arrays, ultrasonic transducers, microwave electrodes, and ohmically heated hot wires, and such devices may be substituted for the electrodes 48, 50.

The ablation/mapping catheter 14 further comprises temperature sensors (not shown), such as thermocouples or thermistors, which may be located on, under, abutting the longitudinal end edges of, or in between, the electrodes 48, 50. In some embodiments, a reference thermocouple (not shown) may also be provided. For temperature control purposes, signals from the temperature sensors are transmitted to the RF generator 18 by way of wires (not shown) that are also connected to the aforementioned PC board in the handle 26. Suitable temperature sensors and controllers, which control power to electrodes based on a sensed temperature, are disclosed in U.S. Pat. Nos. 5,456,682, 5,582,609 and 5,755,715.

In the illustrated embodiment, the mapping element 24 takes the form of a pair of ring electrodes 52, 54 that are mounted on the medial section 42 of the distal member 30. Optionally, additional pairs of ring electrodes may be located along the distal member 30. The mapping electrodes 52, 54 are composed of a solid, electrically conducting material, like platinum or gold, attached about the catheter body 20. Alternatively, the mapping electrodes 52, 54 can be formed by coating the exterior surface of the catheter body 20 with an electrically conducting material, like platinum or gold. The coating can be applied using sputtering, ion beam deposition, or equivalent techniques. The mapping electrodes 52, 54 can have suitable lengths, such as between 0.5 and 5 mm. In use, the mapping electrodes 52, 54 sense electrical events in myocardial tissue for the creation of electrograms, and are electrically coupled to the mapping processor 16 (shown in FIG. 1). A signal wire 54 (shown in FIGS. 10-12) is electrically coupled to each mapping electrode 52, 54. The wires 54 extend through the catheter body 20 into an external multiple pin connector (not shown) located on the handle 26, which electrically couples the mapping electrodes 52, 54 to the mapping processor 16.

II. Localization Subsystem

Referring back to FIG. 1, the localization subsystem 6 includes a plurality of tracking elements 56, a plurality of reference elements 58, and a controller/processor 60 coupled to the reference elements 58 and tracking elements 56. As shown in the ablation/mapping subsystem 4 illustrated in FIG. 1, the tracking elements 56 (in this case, a proximal element 56(1), a medial element 56(2), and a distal element 56(3)) are carried by the distal member 30 of the mapping/ablation catheter 14. Significantly, the proximal tracking element 56(1) is located at the proximal end of the proximal section 40, the medial tracking element 56(2) is located at the proximal end of the medial section 42, and the distal tracking element 56(3) is located at the proximal end of the distal section 44, as illustrated in FIGS. 2 and 3.

At least some of the reference elements 58 are carried by a pair of reference catheters (not shown). The distal end of each reference catheter may optionally comprise a plurality of electrodes (not shown), e.g., to provide the reference catheter with mapping functionality. The reference catheters may be affixed within selected regions of the heart, in order to establish an internal three-dimensional coordinate system, as will be further discussed below. Alternatively, the reference elements 58 may be located outside of the patient's body, e.g., affixed to the patient's skin, in order to establish an external three-dimensional coordinate system.

In any event, the controller/processor 60 can establish a three-dimensional coordinate system by controlling and processing signals transmitted between the spaced apart reference elements 58. In essence, the three-dimensional coordinate system provides an absolute framework in which all spatial measurements will be taken. The controller/processor 60 can also determine the positional coordinates of the tracking elements 56, and thus the distal end of the mapping/ablation catheter 14, within this coordinate system. As will be described in further detail below, this positional information can ultimately be used to graphically reconstruct a chamber of the heart, as well as the valves and vessel ostia of the heart. The positional information will also ultimately be used to graphically reconstruct the distal end of the mapping/ablation catheter 14 (as well as any reference catheters), track the movement of the mapping/ablation catheter 14 within the heart chamber, heart valves, and vessel ostia, and, in conjunction with the mapping data obtained from the mapping processor 16, generate an electrophysiological map.

In the illustrated embodiment, the localization subsystem 6 employs ultrasound triangulation principles to determine the coordinates of the tracking elements 56 carried by the mapping/ablation catheter 14. In this case, the location and reference elements 56, 58 take the form of ultrasound transducers. The coordinates of the tracking elements 56 can be determined within an internal reference frame established by arranging the reference elements 58 in three-dimensional space. For example, the first two dimensions of the coordinate system can be provided by placing a reference catheter within the coronary sinus (CS) (not shown) of the heart, thereby disposing its reference elements 58 in a two-dimensional plane. The third dimension can be provided by placing another reference catheter within the right ventricular (RV) apex (not shown) of the heart to dispose its reference elements 58 off of the two-dimensional plane. Notably, only four reference elements 58 are needed to provide the three dimensions. Any remaining reference elements 58 can be used to improve the accuracy of the triangulation process.

The controller/processor 60 is operated to sequentially transmit ultrasound pulses (e.g., 500 KHz pulses) through each reference element 58, and then measure the time delay between the respective transmit and receive pulses at the tracking element 56 and other reference elements 58. The controller/processor 60 then calculates the relative distances between each reference element 58 and the remaining reference elements 58 and tracking elements 56 using the "time of flight" and velocity of the ultrasound pulses. The distance information can be calculated as d=vt, where d is the distance between the transmitter and receiver, v is the velocity of the ultrasound signal within the medium (i.e., blood), and f is the time delay. To simplify the distance computations, the velocity of the ultrasound pulses may be assumed to be constant. This assumption typically only produces a small error when the reference elements 58 are located inside the body, since the velocity of ultrasound propagation is approximately the same in body tissue and blood.

The controller/processor 60 then establishes a three-dimensional coordinate system by triangulating the distances between the reference elements 58, and determines the positions of each of the tracking elements 56 within that coordinate system by triangulating the distances between the reference elements 58 and the tracking elements 56. Additional details on determining the positions of ultrasound transducers within a three-dimensional coordinate system can be found in U.S. Pat. No. 6,490,474 and U.S. patent application Ser. No. 09/128,304, entitled "A dynamically alterable three-dimensional graphical model of a body region," which are fully and expressly incorporated herein by reference.

It should be noted that there are other means for determining the positions of catheters within a three-dimensional coordinate system. For example, magnetic tracking techniques, such as that disclosed in U.S. Pat. No. 5,391,199, which is expressly incorporated herein by reference, can be employed. As another example, a voltage tracking technique, such as that disclosed in U.S. Pat. No. 5,983,126, which is expressly incorporated herein by reference, can be employed.

III. Graphical User Interface

Figure 16:
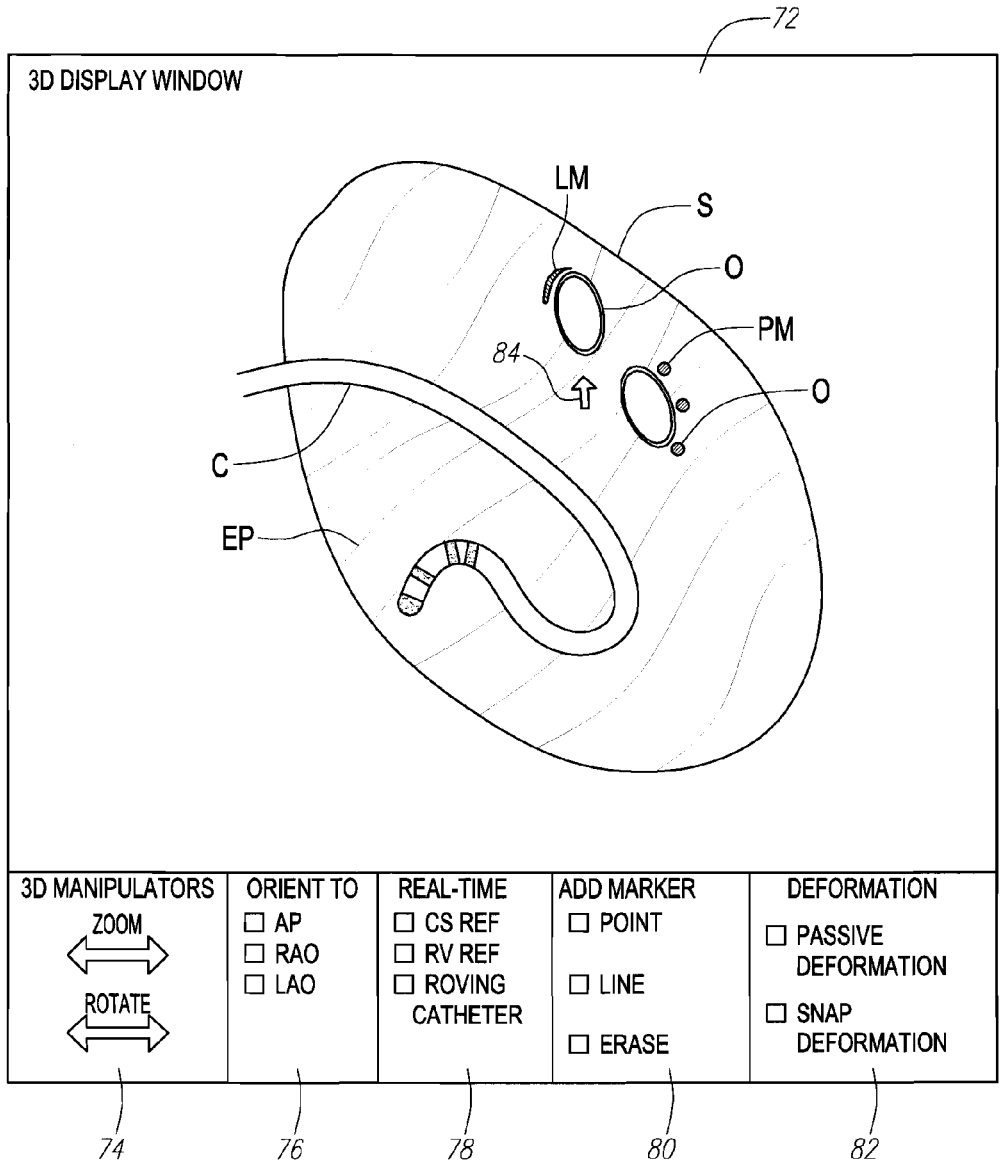
FIG. 16 is a front view of monitor displaying graphical representations of the ablation/mapping catheter of FIGS. 2 and 3, the endocardial surface of the left atrium of the heart, and a superimposed electrical activity map.

Referring still to FIG. 1, the graphical user interface 8 comprises a graphical processor 62, a user input device 64, and an output device 66 (and specifically, a monitor). The graphical processor 62 is configured for generating a representation of the surface of an internal anatomical structure (in this case, the endocardial surface within the left atrium of the heart, including the ostium O of selected pulmonary veins) in the form of a computer-generated graphical representation S, which is then displayed in a 3-D display window 72 on the monitor 66, as illustrated in FIG. 16. The three-dimensional graphical processor 62 accomplishes this by acquiring the positions of the tracking elements 56 within the global coordinate system from the localization subsystem 6 as the mapping/ablation catheter 14 is moved around within the cavity of the left atrium, including the ostia of the pulmonary veins, and then deforming the surface representation S (in particular, an anatomical shell) to the position of the distal tip of the catheter 14, which is extrapolated from the acquired positions of the tracking elements 56 and the known geometry of the catheter 14.

As will be described in further detail below, the surface representation S can be initially deformed to include interior points (i.e., points periodically acquired, e.g., once every heart, while the catheter 14 is moved around in the left atrium) and subsequently refined to include surface points (i.e., points taken at designated times when the distal catheter tip is touching the endocardial surface of the left atrium). Although only the endocardial surface within the left atrium is shown reconstructed in FIG. 16, it should be noted that the other chambers (right atrium and left and right ventricles) of the heart can be graphically reconstructed in the same manner by moving the distal end of the catheter 14 within the respective chambers to acquire interior and surface points.

In addition to generating graphical representations of anatomical structures, the graphical processor 62 is also configured for generating a graphical representation C of the mapping/ablation catheter 14 within the established coordinate system, which is then superimposed over the graphical heart representation S in the 3D display window 72, as illustrated in FIG. 16. The graphical processor 62 can generate the graphical catheter model C from a pre-stored graphical model of the catheter 14, which can be deformed in accordance with the calculated positional coordinates of the tracking elements 56 carried by the catheter 14. In the illustrated embodiment, the graphical catheter representation C is dynamically generated in real-time. That is, the catheter representation C is graphically generated in successive time periods (e.g., once every heartbeat), so that it moves and bends as the actual catheter 14 is moved and bent within the heart chamber. The graphical processor 62 may optionally be configured to generate graphical representations of the reference catheters (not shown) in real-time.

The graphical processor 62 is also configured for generating an electrical activity map EP within the established coordinate system, which is then superimposed over the graphical heart representation S in the 3D display window 72, as illustrated in FIG. 16. The graphical processor 62 can generate the electrical activity map EP based on the electrical activity information acquired from the ablation/mapping subsystem 4 and the positions of the mapping electrodes 24 geometrically derived from the positions of the tracking elements 56 obtained from the localization subsystem 6. This electrical activity map illustrates sites of interest, e.g., electrophysiology recording and ablation sites, for providing subsequent ablative treatment, and can be provided in the form of an isochronal or isopotential map. The electrical activity information may also be displayed separately from the 3D display window 72.

Additional details on graphically generating heart chambers, catheters, and electrical activity maps within a three-dimensional environment can be found in U.S. Pat. No. 6,490,474 and U.S. patent application Ser. No. 09/128,304, entitled "A dynamically alterable three-dimensional graphical model of a body region," which have previously been incorporated herein by reference.

The user input device 64 allows the user to interact with the graphics displayed on the monitor 66, and comprises a standard keyboard 68 and a graphical pointing device 70, such as a mouse. The graphical processor 62 responds to the user input device 64 by manipulating the graphics within the 3D display window 72. As an example, the user may rotate the 3D display window 72 in three-dimensions and "zoom" towards or away from the window 72 by clicking on the appropriate icon in the manipulation box 74 using the mouse 70. The user may also select one of the standard orientations, used in fluoroscopy, such as anterior-posterior (AP), lateral, right anterior oblique (RAO) or left anterior oblique (LAO) by selecting the appropriate icon in orientation box 76 using the mouse 70. The user may also select which catheters to display in real-time by checking the appropriate icons in the real-time box 78 using the mouse 70.

Using the mouse 70, the user can also mark anatomical regions of interest on the heart model by placing a cursor 84 at the appropriate location on the surface representation S and clicking. In the illustrated embodiment, the user can either mark the endocardial surface representation S with point markings PM or with line markings LM (either linear or curvilinear). For example, if the user desires to place a point marking PM at an anatomical region of interest, the appropriate icon in the marking box 80 can be clicked, and then the user can mark the surface representation S by moving the cursor 84 to a selected region on the surface representation S and clicking the mouse 70. The surface representation S can be marked with additional point markings PM in the same manner. If the user desires to place a line marking LM at an anatomical region of interest, the appropriate icon in the marking box 80 can be clicked, and then the user can mark the surface representation S by clicking the mouse 70, and dragging the cursor 84. If curvilinear, the line marking LM may either be open or closed. The user may also erase marks PM/LM from the surface representation S by clicking on the appropriate icon in the marking box 80, and them moving the cursor 84 over the mark PM/LM, while clicking the mouse 70. Point/line markings PM/LM can also be automatically marked on the surface representation S each time ablation energy is delivered to the ablation electrodes 48, 50, thereby allowing the user to automatically keep track of the lesions. For example, a point marking PM can be created when a discrete lesion is created, and a line marking LM can be created when a continuous line lesion is created.

The user may also select whether the graphical processor 62 performs "passive chamber deformation," which deforms the surface representation S outward to include outerlying interior points acquired by the catheter 14 over successive time periods (e.g., every heart beat) or "snap deformation," which deforms the anatomical shell to a surface point acquired by the catheter 14 (preferably, somewhere on the endocardial surface) when designated by the user. The user may click the "Passive Deformation" icon in the deformation box 82 using the mouse 70 to prompt the graphical processor 62 to perform passive chamber deformation as the distal end of the catheter 14 is moved within the left atrium of the heart, or may click the "Snap Deformation" icon in the deformation box 82 using the mouse 70 to prompt the graphical processor 62 to perform snap deformation each time the distal catheter tip is placed into contact with the endocardial surface of the left atrium.

Having described the structure of the treatment system 2, its operation in creating a circumferential lesion within the ostium O of a pulmonary vein PV, thereby electrically isolating arrhythmia causing substrates within the pulmonary vein PV from the left atrium LA of the heart H, will now be described with reference to FIGS. 17A-17J. It should be noted that the views of the heart H and other interior regions of the body described herein are not intended to be anatomically accurate in every detail. The figures show anatomic details in diagrammatic form as necessary to show the features of the embodiment described herein.

First, under fluoroscopy, the reference catheters are intravenously introduced into the heart, and in particular, within the coronary sinus (CS) and right ventricle (RV) apex, so that the reference elements 58 are fixed within a three-dimensional arrangement (reference catheters not shown). The guide sheath 12, or another guide sheath, can be used to introduce the reference catheters into the desired locations of the heart. During introduction of the reference catheters, the localization subsystem 6 may be operated to transmit signals between the reference elements 58, so that the locations of the distal ends of the reference catheters can be determined and graphically displayed in the 3D display window 72 on the monitor 66. [0081] Next, the guide sheath 12 is introduced into the left atrium LA of the heart H (FIG. 17A). Introduction of the guide sheath 12 within the left atrium LA can be accomplished using a conventional vascular introducer retrograde through the aortic and mitral valves, or can use a transseptal approach from the right atrium, as illustrated in FIG. 17A. A guide catheter or guide wire (not shown) may be used in association with the guide sheath 12 to aid in directing the guide sheath 12 through the appropriate artery toward the heart H. Of course, the guide sheath 12 can be introduced into other chambers of the heart H, such as the left ventricle, e.g., if the disease to be treated is ventricular tachycardia.

Once the distal end of the guide sheath 12 is properly placed, the ablation/mapping catheter 14 is introduced through the guide sheath 12 until the distal member 30 is deployed from the guide sheath 12 (FIG. 17B). As can be seen, the curvable section of the catheter body 20, and in particular the proximal section 40, is automatically placed into its curved geometry (i.e., it forms the curve C1 with the apex A1) due to its pre-shaped nature. Alternatively, if the catheter 12 is steerable, the steering mechanism can be manipulated to subsequently place the proximal section 40 into its curved geometry when desired. In any event, during the introduction of the catheter 14, the localization subsystem 6 may be operated to transmit signals between the reference elements 58 and the tracking elements 54, so that the locations of the distal end of the catheter 14 can be determined and graphically displayed in the 3D display window 72.

The graphical processor 62 is then operated in the "Passive Deformation" mode, and the catheter 14 is moved around within the left atrium LA as the position of the distal catheter tip is determined. As a result, the graphical processor 62 generates the surface representation S (shown in FIG. 16), which begins as a generally spherical shape, and deforms it to include the interior anatomical points that are acquired by the catheter 14 outside of the endocardial surface representation S (shown in FIG. 16). The graphical processor 62 can then be operated in the "Snap Deformation" mode to refine the surface representation S, in which case, the distal tip of the catheter 14 will be placed against selected regions of the endocardial surface, so that the graphical processor 62 can deform the surface representation S to the surface points acquired by the distal catheter tip. During its deformation in both Passive Deformation and Snap Deformation modes, the surface representation S is displayed in the 3D display window 72 on the monitor 66. Alternatively, rather than use the catheter 14 to acquire points for graphically generating the representation S, a separate catheter having the same localization capabilities as the catheter 14 can be used to acquire the points. [0084] Next, the catheter 12 is retracted into the sheath 12, and the distal end of the sheath 12 is placed adjacent a selected pulmonary vein PV (FIG. 17C). Once the guide sheath 12 is properly placed, the distal member 30 of the catheter 14 is deployed from the guide sheath 12 (FIG. 17D). The apex A1 of the curve C1 is then inserted into the ostium O of the pulmonary vein PV until the intermediate/distal sections 42, 44, and in particular, the ablative element 22 and mapping element 24, are placed into contact with tissue sites adjacent the ostium O (FIGS. 17E-1 and 17E-2). As can be seen, the curve C2 of the medial section 42 directs the distal section 44 towards the tissue outside of the ostium O, and the curve C3 of the medial section 42 places the distal section 44 in a non-radial relationship, and specifically a tangential relationship, with the ostium O.

Notably, the resiliency of the medial section 42 of the distal member 30 places the ablative/mapping elements 22, 24 in firm and stable contact with the tissue sites. Also, because the distal member 30 comprises a radio-opaque substance, the relative locations of the portions of the proximal section 40 on either side of the apex A1 will provide the operator with an indication of the extent to which the curve C1 is placed within the pulmonary vein O, and thus, an indication of the location of the ablative/mapping elements 22, 24 relative to the ostium O. That is, the angle between the proximal section portions decreases as the depth of the curve C1 within the ostium O increases. Knowledge of this depth provides an indication of the location of the ablative/mapping elements 22, 24 relative to the ostium O.

Next, the localization subsystem 6 is operated in the "Passive Deformation" and/or "Snap Deformation" mode and the curve C1 rotated within the ostium O to place the catheter distal tip at various sites around the ostium O, thereby collecting points for which the graphical processor 62 can use to graphically generate a representation of the ostium O (shown in FIG. 16) within the graphical endocardial surface representation S.

Notably, if a steering mechanism is provided, the radius of curvature of the curve C1 can be decreased (FIGS. 17F-1 and 17F-2), thereby preventing the resiliency of the distal member 30 from causing the curve C1 to grab the inner surface of the pulmonary vein PV as it is rotated. In the illustrated method, decreasing the radius of curvature of the curve C1 deflects the medial section 42 towards the proximal end of the proximal section 40 (in the direction of the arrow) a distance of about Vi inch to fully release the curve C1 from the inner surface of the pulmonary vein PV. The steering mechanism can also be operated to allow the resiliency of the distal member 30 to passively increase the radius of curvature of the curve C1 (e.g., by removing the tension created by the steering mechanism), so that the curve C1 reengages the inner surface of the pulmonary vein PV. In the case where the steering mechanism provides the sole means for deflecting the proximal section 40, the radius of curvature of the curve C1 can be actively increased via operation of the steering mechanism. This iterative curve C1 decreasing, curve C1 rotation, and curve C1 increasing technique can be used during mapping and ablation of the tissue adjacent the ostium O in order to place the ablative/mapping elements 22/24 is firm contact with different tissue sites described below.

Once the graphical representation of the ostium O has been created, the mapping processor 16 (shown in FIG. 1) is operated in order to obtain and record ECG signals from the ostium, with the ablative element 22 serving as a mapping element to measure ECG signals outside of the ostium O, and the mapping element 24 serving to measure ECG signals inside of the ostium O. As described below, these ECG signals will be compared with the ECG signals obtained subsequent to an ablation procedure in order to determine if the resultant lesion has successfully electrically isolated the arrhythmia causing substrates from the left atrium LA of the heart H. Additional tissue sites can be mapped by rotating the curve C1 within the ostium O about the apex A1 to place the ablation/mapping elements 22, 24 in contact with other tissue sites, and operating the mapping processor 16.

Once the pre-ablation ECG signals have been obtained and recorded, the ablative element 22 is placed in contact with a first tissue site S1 (FIG. 17G). This can be accomplished simply by leaving the curve C1 in place after mapping has been completed or by rotating the curve C1 within the ostium O about the apex A1 to place the ablative element 22 into contact with a different tissue site at which the last mapping procedure was performed.

The RF generator 18 (shown in FIG. 1) is then operated in order to convey RF energy to the ablative element 22 (either in the monopolar or bipolar mode), thereby creating a linear lesion L1 (FIG. 17H). As can be seen, the linear lesion L1 is tangential to the perimeter of the ostium O, thereby maximizing the span of the lesion L1 about the ostium O and the effectiveness of the lesion L1 in blocking the errant electrical pathways from the pulmonary vein PV. Alternatively, the linear lesion L1 may be somewhat oblique to the perimeter of the ostium O, but preferably does not deviate more than 30 degrees from the tangent to the ostium O.

Next, the curve C1 is again rotated within the ostium O about the apex A1 to place the ablative element 22 into contact with a second tissue site S2 (FIG. 17I). Then, the RF generator 18 is operated again in order to convey RF energy to the ablative element 22, thereby creating another linear lesion L2 (FIG. 17J). As can be seen, the linear lesion L2, like the linear lesion L1, is tangential to the perimeter of the ostium O, thereby maximizing the span of the lesion L2 about the ostium O and the effectiveness of the lesion L2 in blocking the errant electrical pathways from the pulmonary vein PV. In the illustrated method, the location of the second tissue site S2 is selected such that the linear lesions L1 and L2 form a continuous lesion. This ablation process is repeated until the entire ostium O is encircled with a circumferential lesion. Alternatively, if the locations of the arrhythmia causing substrates are known, the tissue sites S can be selected, such that discrete linear lesions L are formed around the ostium O at strategic locations.

As can be appreciated, formation of the lesions L around the ostium O can be more controlled and predefined, since movement of the ablative element 22 is limited to a circle having a point at the apex A1 of the curve C1. This can be contrasted with the previous "free-hand" approach where movement of the ablative element 22 is unlimited and difficult to control. In addition, the unique design of the distal member 30 ensures that the ablative element 22 is kept out of the PV where irreparable damage can be caused.

After the lesion has been created, the mapping processor 16 is again operated to obtain and record ECG signals from the PV. These post-ablation ECG signals are compared to the pre-ablation ECG signals to determine whether the circumferential lesion has completely isolated the arrhythmia causing substrates in the pulmonary vein PV from the LA of the heart H. Once proper ablation has been confirmed, the guide sheath 12 and ablation/mapping catheter 14 are removed from the patient's body, or alternatively, are used to create a circumferential lesion within another pulmonary vein.

Although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present invention as defined by the claims.

What is claimed is:

1. A method of performing a medical procedure on tissue adjacent an ostium of an anatomical vessel, comprising:
   providing a catheter having an elongated flexible catheter body including a proximal shaft portion and a distal shaft portion having a proximal section pre-shaped to form a simple curve having an apex sized to be inserted into the vessel ostium, a medial section pre-shaped to form a complex curve, and a distal section configured to contact the adjacent tissue when the curve apex is inserted within the vessel ostium, the catheter including at least one tracking element carried by the distal shaft portion;
   inserting the catheter into the vessel with the simple curve inserted into the ostium and the distal section in contact with a first tissue site; and
   rotating the simple curve within the vessel about the curve apex to place the distal section in contact with a second tissue site.

2. The method of claim 1, wherein after the step of inserting the catheter into the vessel, the method further comprises performing a first medical procedure with the catheter.

3. The method of claim 2, wherein after the step of rotating the simple curve, the method further comprises performing a second medical procedure with the catheter.

4. The method of claim 3, wherein the first and second medical procedures include determining a location of the at least one tracking element.

5. The method of claim 3, wherein the catheter comprises a therapeutic element carried by the distal section, and at least one of the first and second medical procedures includes performing therapy with the therapeutic element at the first or second tissue site.

6. The method of claim 5, wherein the therapeutic element comprises a tissue ablative element, and the step of performing therapy comprises delivering ablation energy to the ablative element to create a lesion at the first or second tissue site.

7. The method of claim 3, wherein the catheter comprises a tissue mapping element, and the method further comprises receiving mapping signals from the mapping element to create a mapping data point at the first or second tissue site.

8. The method of claim 1, wherein the vessel is a pulmonary vein.

9. A method of performing a medical procedure adjacent an anatomical vessel using a catheter having a proximal section and a distal section, comprising:
   forming the proximal section into a simple curve having an apex;
   inserting the simple curve apex into the vessel ostium to place the distal section in contact with a first tissue site adjacent the vessel ostium:
   rotating the simple curve within the vessel about the curve apex while the curve apex is in the vessel ostium to place the distal section in contact with a second tissue site adjacent the vessel ostium.

10. The method of claim 9, wherein the distal section is placed into a non-radial relationship with the vessel ostium when the curve apex is inserted into the vessel ostium.

11. The method of claim 9, wherein the distal section further has a medial section, the method further comprising forming the medial section into a complex curve that bends in a direction opposite the simple curve.

12. The method of claim 11, wherein the complex curve bends in a direction opposite to and out-of-plane with the simple curve.

13. The method of claim 9, wherein after the step of inserting the simple curve apex into the vessel ostium, the method further comprises performing a first medical procedure with the catheter.

14. The method of claim 13, wherein after the step of rotating the simple curve, the method further comprises performing a second medical procedure with the catheter.

15. The method of claim 14, wherein the catheter further comprises at least one tracking element carried by the distal section, wherein the first and second medical procedures include determining a location of the at least one tracking element.

16. The method of claim 14, wherein the catheter comprises a therapeutic element carried by the distal section, and at least one of the first and second medical procedures includes performing therapy with the therapeutic element at the first or second tissue site.

17. The method of claim 16, wherein the therapeutic element comprises a tissue ablative element, and the step of performing therapy comprises delivering ablation energy to the ablative element to create a lesion at the first or second tissue site.

18. The method of claim 14, wherein the catheter comprises a tissue mapping element, and the method further comprises receiving mapping signals from the mapping element to create a mapping data point at the first or second tissue site.

19. The method of claim 9, wherein the vessel is a pulmonary vein.

* * * * *